(12) United States Patent
Barberio

(10) Patent No.: US 8,012,112 B2
(45) Date of Patent: *Sep. 6, 2011

(54) ORTHOPEDIC BRACES AND CASTS WITH AERATING ARRANGEMENTS

(76) Inventor: Alessandro Aldo Barberio, Aurora (CA)

( * ) Notice: Subject to any disclaimer, the term of this patent is extended or adjusted under 35 U.S.C. 154(b) by 453 days.

This patent is subject to a terminal disclaimer.

(21) Appl. No.: 11/353,067

(22) Filed: Feb. 14, 2006

(65) Prior Publication Data

US 2007/0191749 A1    Aug. 16, 2007

(51) Int. Cl.
A61F 5/00    (2006.01)
(52) U.S. Cl. .............. 602/14; 602/16; 602/23; 602/27; 36/15; 36/42
(58) Field of Classification Search .......... 602/1, 5, 602/6, 13, 14, 20, 23, 27; 36/15, 42
See application file for complete search history.

(56) References Cited

U.S. PATENT DOCUMENTS

| | | | |
|---|---|---|---|
| 1,142,662 A * | 6/1915 | Blaney | 36/36 R |
| 1,213,941 A | 1/1917 | Patrick | |
| 2,480,035 A | 8/1949 | Lindstrom | |
| 2,666,207 A | 1/1954 | Lucas | |
| 2,704,067 A | 3/1955 | Moses | |
| 2,731,963 A | 1/1956 | Blank | |
| 2,822,806 A | 2/1958 | Blank | |
| 3,116,731 A | 1/1964 | Baxter | |
| 3,307,537 A | 3/1967 | Simon | |
| 3,307,545 A | 3/1967 | Surowitz | |
| 3,417,408 A | 12/1968 | Caggiano | |
| 3,631,854 A | 1/1972 | Fryer | |
| 3,656,477 A | 4/1972 | Thomas | |
| 3,680,550 A | 8/1972 | Tunstall | |
| 3,701,349 A | 10/1972 | Larson | |
| 3,882,857 A | 5/1975 | Woodall, Jr. | |
| 3,930,496 A | 1/1976 | Gibbons | |
| 3,955,565 A * | 5/1976 | Johnson, Jr. | 602/12 |
| 3,998,220 A | 12/1976 | Cleer, Jr. | |
| 4,019,506 A | 4/1977 | Eschmann | |
| 4,308,862 A | 1/1982 | Kalmar | |
| 4,387,710 A | 6/1983 | Beatty | |
| 4,461,289 A | 7/1984 | Didier et al. | |

(Continued)

FOREIGN PATENT DOCUMENTS

CA    2447487    4/2004

(Continued)

*Primary Examiner* — Patricia M Bianco
*Assistant Examiner* — Keri J Nelson
(74) *Attorney, Agent, or Firm* — Young Basile Hanlon & MacFarlane PC

(57) ABSTRACT

A brace for providing therapeutic pressure to a person's or animal's body part is provided together with a venting device for use with a cast or brace. The brace has a rigid exterior shell which is perforated over a substantial portion of its surface. An interior resilient liner is arranged in the shell and this liner is also perforated. At least a portion of the liner has two inner and outer layers of flexible material and spacer members connecting these layers and forming air passageways. At least the inner layer is porous. The venting device can have two half sections which, when combined together, enclose a body part. Each half section is preformed to closely fit around a curved side of the body part and has spaced-apart inner and outer layers of flexible, material with at least the inner layer being porous. Again, spacer members are arranged between and connect these layers and form air passageways.

7 Claims, 11 Drawing Sheets

U.S. PATENT DOCUMENTS

| | | | |
|---|---|---|---|
| 4,621,624 A | | 11/1986 | Rayboy |
| 4,898,160 A | | 2/1990 | Brownlee |
| 5,018,515 A | | 5/1991 | Gilman |
| 5,078,128 A | | 1/1992 | Grim et al. |
| 5,086,518 A | | 2/1992 | Staley |
| 5,167,613 A | | 12/1992 | Karami et al. |
| 5,226,194 A | | 7/1993 | Staley |
| 5,370,133 A | * | 12/1994 | Darby et al. ............ 602/23 |
| 5,433,695 A | | 7/1995 | Drennan |
| 5,511,323 A | | 4/1996 | Dahlgren |
| 5,577,998 A | * | 11/1996 | Johnson et al. ............ 602/5 |
| 5,628,283 A | | 5/1997 | Huegelmeyer |
| 5,779,656 A | | 7/1998 | Goto |
| 5,800,369 A | | 9/1998 | Goto |
| 5,836,902 A | * | 11/1998 | Gray ............ 602/5 |
| 5,857,987 A | * | 1/1999 | Habermeyer ............ 602/23 |
| 5,891,067 A | | 4/1999 | Reed |
| 5,916,184 A | | 6/1999 | McKeel |
| 6,093,161 A | * | 7/2000 | Vlaeyen et al. ............ 602/6 |
| 6,228,044 B1 | * | 5/2001 | Jensen et al. ............ 602/27 |
| 6,311,413 B1 | * | 11/2001 | Chern et al. ............ 36/15 |
| 6,361,514 B1 | * | 3/2002 | Brown et al. ............ 602/23 |
| 6,547,751 B1 | | 4/2003 | Barberio |
| 6,616,622 B1 | | 9/2003 | Barberio |
| 6,689,081 B2 | * | 2/2004 | Bowman ............ 602/27 |
| 7,250,034 B2 | * | 7/2007 | Barberio ............ 602/14 |
| 2002/0128574 A1 | * | 9/2002 | Darby ............ 602/23 |
| 2004/0162511 A1 | | 8/2004 | Barberio |
| 2004/0230148 A1 | * | 11/2004 | Barberio ............ 602/3 |
| 2005/0171461 A1 | * | 8/2005 | Pick ............ 602/27 |

FOREIGN PATENT DOCUMENTS

| | | |
|---|---|---|
| CA | 2467154 | 11/2004 |
| CA | 2467154 A1 * | 11/2004 |

\* cited by examiner

ORTHOPEDIC BRACES AND CASTS WITH AERATING ARRANGEMENTS

This invention relates to braces for supporting and putting pressure on a person's or animals' body part, venting devices for use with orthopedic casts or braces, and supporting and ventilating devices for a walking cast.

In order to treat certain injuries in the lower extremities of a human's or animal's body, such as a bone fracture or severe sprain, it is known to immobilize the region of the injured body part completely by the use of a molded plaster or resin cast. However, once the injured body part has begun to heal and has stabilized, it is known that a more rapid recovery can sometimes be obtained by gradually and progressively permitting the injured body part to bear some weight and to undergo some exercise. In the latter stage of recovery, an orthopedic brace may be used.

In one such known brace, there is a shaped rigid outer shell on the inside of which is provided an inflatable liner or air cell to engage and to apply pressure to the body part or limb. For example, in the brace of U.S. Pat. No. 5,577,998 issued Nov. 26, 1996 to Aircast, Inc., the brace includes a rear outer shell member having a vertical portion that extends up the lower part of the user's leg and a horizontal portion that extends under the foot, a frontal outer shell member that covers the front of the lower leg and the top of the foot, and air cells disposed within a liner of the brace. Flexible straps are used to secure the rear and frontal shell members securely about the lower leg and foot. Using a brace of this type, the ankle and leg are sufficiently supported that the wearer of the brace can walk. Because the wearer is able to walk and carry out certain allowed exercises, this can lead to a more rapid complete healing of the injured part than would be the case if such a brace were not used.

A common and well known problem with the use of rigid casts made of plaster or fiberglass is the lack of ventilation to the skin area under the cast and this can also be a problem with a brace, particularly when the liner of the brace is not constructed in a fashion to provide adequate air ventilation. A lack of air to the skin area can cause discomfort and irritation to the patient. A variety of different structures and methods have been proposed in the past for providing air ventilation to the skin under a cast. It is known, for example, to provide cast venting devices in the form of a woven fabric with an elongate tube or similar air passageway in contact with the skin and over which the plaster of paris mix or fiberglass casting material can be placed to form the cast. Also, it is known to provide a device for forcing air under the cast, one such device being an air pump equipped with a suitable delivery mechanism.

In my co-pending Canadian patent application No. 2,467,154 filed May 12, 2004, there is described an improved cast venting device that may comprise either two elongate strips or two layers of flexible material, at least one of these layers being porous. The strips or layers are spaced apart from each other and are parallel. Flexible spacer members are arranged between the strips or layers and connect them together and these members form air passageways between the adjacent spacers. A preferred material for the inner porous layer or both layers is ethyl vinyl acetate (EVA), this material having numerous small holes distributed evenly over its surfaces.

There is described herein a brace for providing therapeutic pressure to a person's or animal's body part, this brace including both a rigid exterior shell and an interior liner which provides air passageways to allow air circulation. Thus, this brace may be more comfortable for a user to wear, particularly for an extended period of time.

There is also described herein a venting device for use with a cast or brace which is made of two half sections that can be combined to enclose the body part. This venting device includes two spaced apart inner and outer layers of flexible resilient material and spacer members arranged between and connecting the two layers. Air passageways are formed between the spacer members.

There is further described herein a supporting and ventilating device for a walking cast that includes a base plate formed with air passageways formed in its top surface and these passageways can allow air to flow through a porous sole layer adapted to cover the base plate.

According to one aspect of the invention, a brace for providing therapeutic pressure to a person's or animal's body part includes a rigid exterior shell adapted to fit around at least a major portion of the body part and having interior and exterior surfaces. The shell is perforated over a substantial portion of each of the interior and exterior surfaces so as to allow air to pass through the shell between the surfaces. An interior resilient liner is arranged in the shell to cushion the body part. The liner includes two spaced-apart inner and outer layers of flexible material that extend substantially parallel to each other and spacer members arranged between and connecting the inner and outer layers. At least the inner layer is porous so as to allow air to pass through the inner layer. The spacer members form air passageways between adjacent spacer members so that air can pass along the passageways to allow air circulation in the liner and through the inner layer during use of the brace. The brace includes at least one connector for securing the brace to the body part.

Preferably at least the inner layer of the liner is elastomeric, is made of ethyl vinyl acetate (EVA), and has numerous holes distributed evenly over inner and outer surfaces thereof and extending through the inner layer.

According to another aspect of the invention, a venting device for use with an orthopedic cast or brace comprises two half sections which form the venting device when combined together to enclose a person's or animal's body part. Each half section has a length extending from one end thereof to an opposite end thereof. Each half section is preformed to fit closely around a respective curved side of the body part and includes two spaced-apart inner and outer layers of flexible resilient material that extends substantially parallel to each other. The resilient material of at least the inner layer is porous. Spacer members are arranged between and connect the two layers and form numerous air passageways between adjacent spacer members so that air is free to pass along the passageways from one or more open ends of the passageways located at least one of the two ends of the half section. In order to use the venting device, the two half sections are placed around the selected body part so that they meet along respective lengthwise extending edges thereof and surround the body part. Then, the cast or brace is applied over the venting device so that the venting device is pressed between the body part and the cast or brace.

In one preferred embodiment, each half section is substantially U-shaped in widthwise cross-section and is bent in the lengthwise direction, thereby permitting the venting device to fit around a bent body part such as an elbow.

According to a further aspect of the invention, a supporting and ventilating device for a walking cast enclosing a foot of a human or animal includes a rigid base plate adapted for mounting in the walking cast. This plate is shaped and sized to support firmly at least a major portion of a sole of the foot. The base plate has a network of open topped air passageways formed in the top surface thereof and an aperture system allows air to flow into and out of these air passageways when the base plate is mounted in the walking cast. A flexible sole layer is adapted to cover substantially the top surface of the base plate. This sole layer is porous to permit air to flow between the air passageways and the top surface of the sole layer.

In one preferred embodiment, the base plate is made of rigid plastic materials and has a rounded bottom that forms a convex surface extending substantially from a heel end to a toe end of the base plate.

Further features and advantages of the present braces and venting devices will become apparent from the following detailed description of preferred embodiments taken in conjunction with the accompanying drawings.

Figure 1:
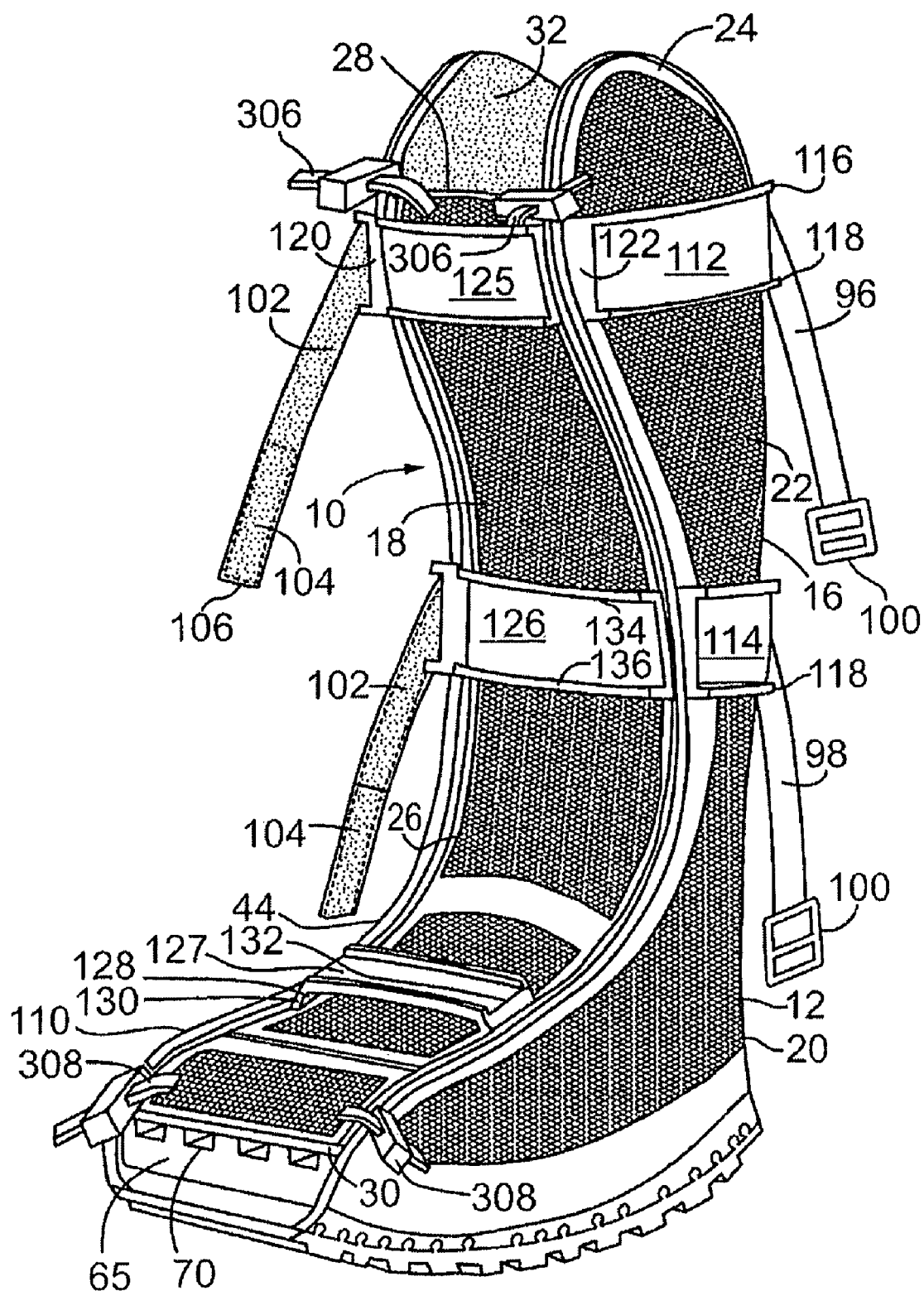
FIG. 1 is a perspective view showing the front and left sides of a walking brace constructed according to the invention.

A preferred form of walking brace 10 for providing therapeutic pressure to a person's body part, namely a lower portion of a person's leg, is shown in FIG. 1. It will be appreciated that although a walking brace is illustrated, it is also possible to employ a brace constructed in accordance with the invention which is not a walking brace but is adapted for use on a body part other than the lower leg. Also although the illustrated walking brace 10 is adapted for use on the lower leg of a person, it will be appreciated by those skilled in the art that a brace constructed in accordance with the invention can also be used on an animal's body part.

Figure 2:
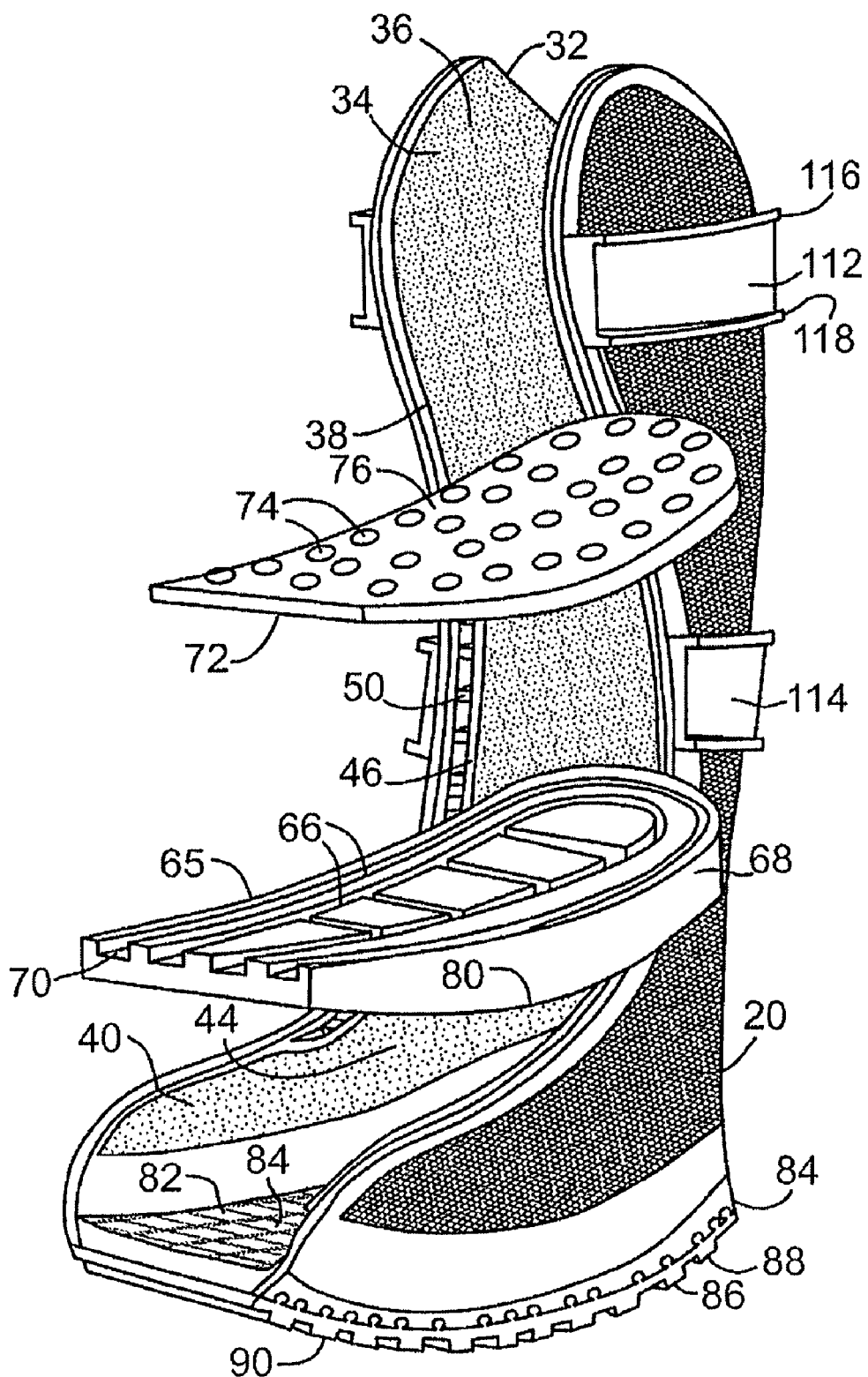
FIG. 2 is a partially exploded perspective view of the walking brace of FIG. 1, this view showing a rigid sole member and a perforated top sole separated from bottom layers of the brace and omitting the frontal section of the brace.
Figure 3:
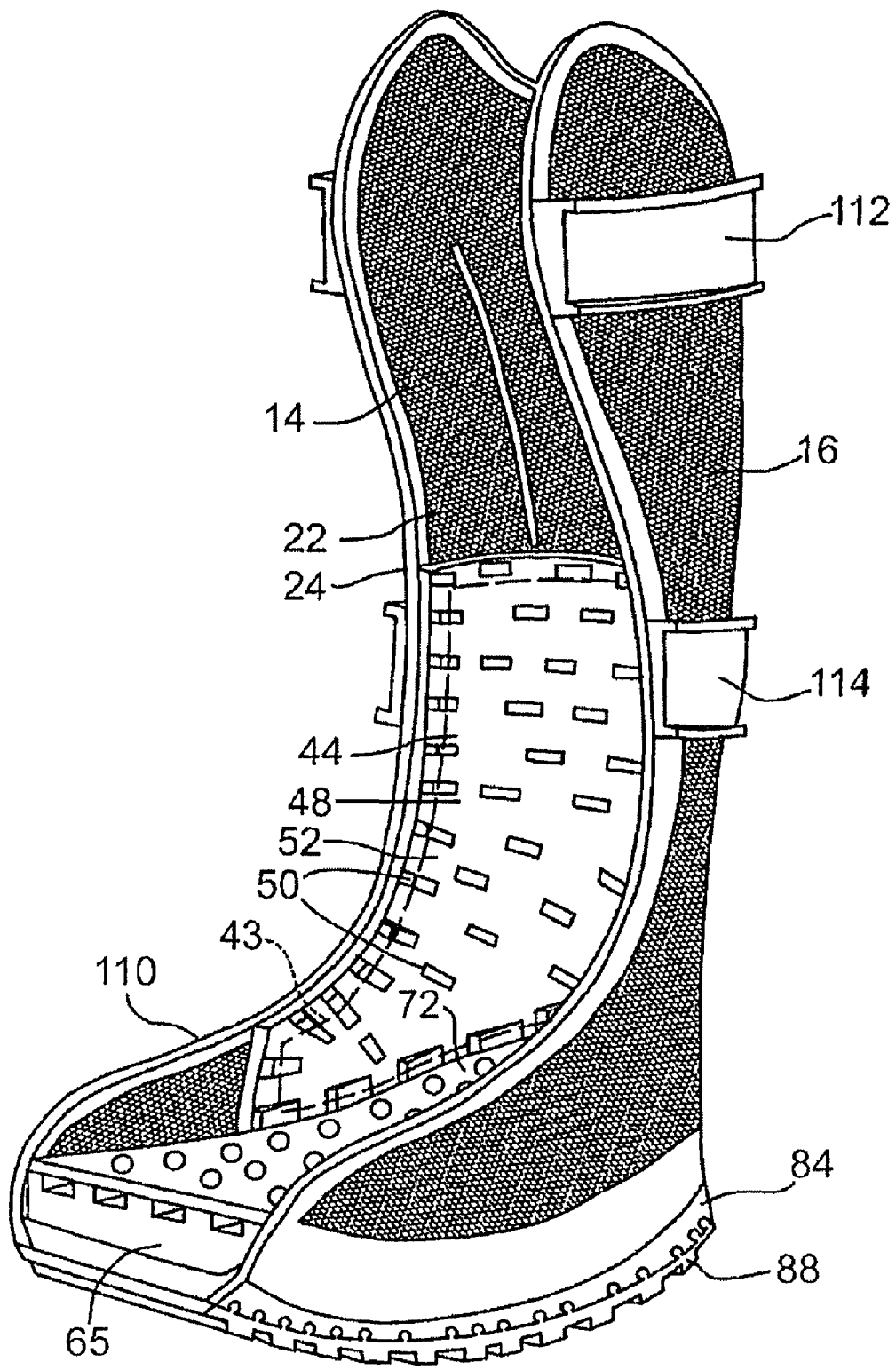
FIG. 3 is a perspective view similar to FIG. 2 but with a layer of an inner liner removed to illustrate underlying support structure, this view omitting the rigid sole member and the top sole.
Figure 4:
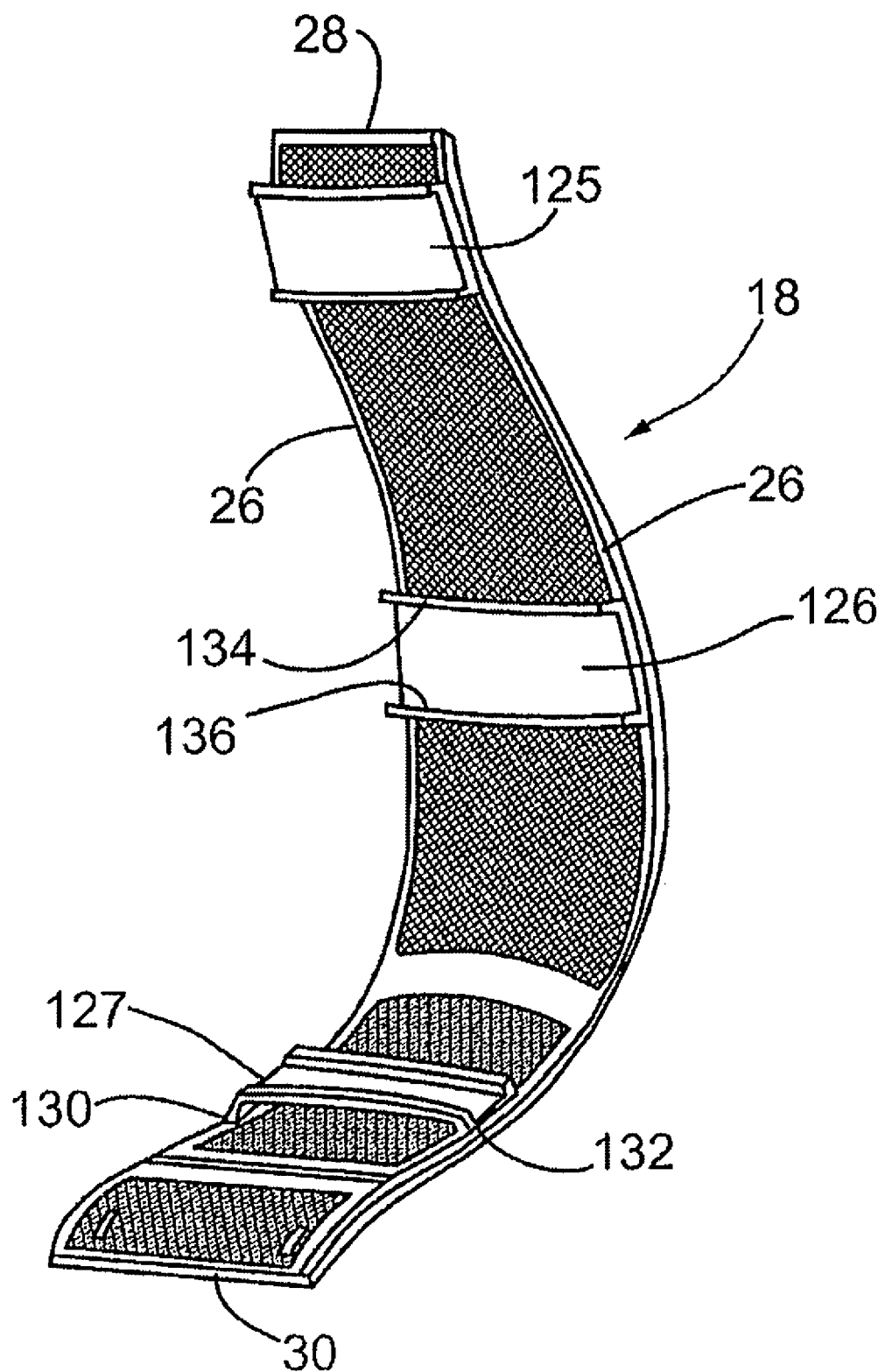
FIG. 4 is a perspective view of the frontal shell that can be used with the walking brace apparatus of FIGS. 1 and 2.

The brace 10 includes a rigid exterior shell indicated generally by reference 12, this shell being adapted to fit around at least a major portion of the body part in this case, the lower portion of a person's leg, including his or her foot, and has an interior surface 14 (visible in FIG. 3) and an exterior surface 16. The preferred exterior shell includes a rigid front shell section 18 adapted to cover a frontal area of the lower leg and a top surface of the foot of a person. This front shell section is detachably secured to a rear shell section 20 shown by itself in FIG. 2. This rear shell section forms the remainder of the exterior shell 12. As shown in FIGS. 1 to 3, the exterior shell, including both the front and rear shell sections 18 and 20, are perforated over a substantial portion of each of the interior and exterior surfaces 14 and 16 so as to allow air to pass through each shell section between these surfaces. These perforations are indicated at 22. Both the front and rear shell sections can be made either from a suitably rigid and tough plastic that can be molded to have the desired perforations or can be made of a suitably strong metal such as aluminum or stainless steel. In either case, the thickness of the shell should be sufficient to provide the required rigidity so that the walls of each shell section will not bend to any significant extent. In other words, each shell section is made sufficiently rigid so that the overall exterior shell can serve its function as a brace that will support the enclosed body part and not permit undesirable movement thereof. The edge section 24 of the rear shell section 20 can be made as a solid plastic or metal strip that is smoothed and rounded so as not to provide a hazard to the user. Similarly, the front shell section 18 can have solid edge strips 26 provided along curved right and left edges and top and bottom solid edge strips 28 and 30.

The walking brace 10 also includes an interior resilient liner 32 arranged in the exterior shell 12 to cushion the body part. The liner 32 is perforated with numerous small passageways 34 over at least a substantial portion thereof so as to allow air to pass readily between the inner surface 36 of the liner and its exterior surface. In the illustrated embodiment, all of the inner surface of the liner is perforated in this manner.

The front shell section 18 can have its inner surface covered with a single layer of the resilient liner material. Also, an upper portion 38 extending to the top of the walking brace and a front portion 40 of the rear shell section 20 can be covered with a single layer of the liner material. This material can be about $\frac{1}{8}^{th}$ inch thick and preferably is elastomeric in nature. One preferred material for this liner is ethyl vinyl acetate (EVA) formed with numerous holes distributed evenly over inner and outer surfaces thereof and extending through the layer. Thus, except for a central portion of this brace (see below), air is able to pass freely through both the perforated outer shell 12 and then through the liner 32. This type of perforated liner is believed to be an improvement over the liner used in the walking brace of U.S. Pat. No. 5,577,998, for example. A difficulty with known liners is that they are made of a soft material which will compress substantially when compressed (as is normal when they are used under a brace). This squeezing and compression of the liner can prevent or substantially reduce any air circulation through the liner. The preferred EVA material is stronger, more sturdy, and less likely to collapse in a way that prevents air circulation.

Figure 18:
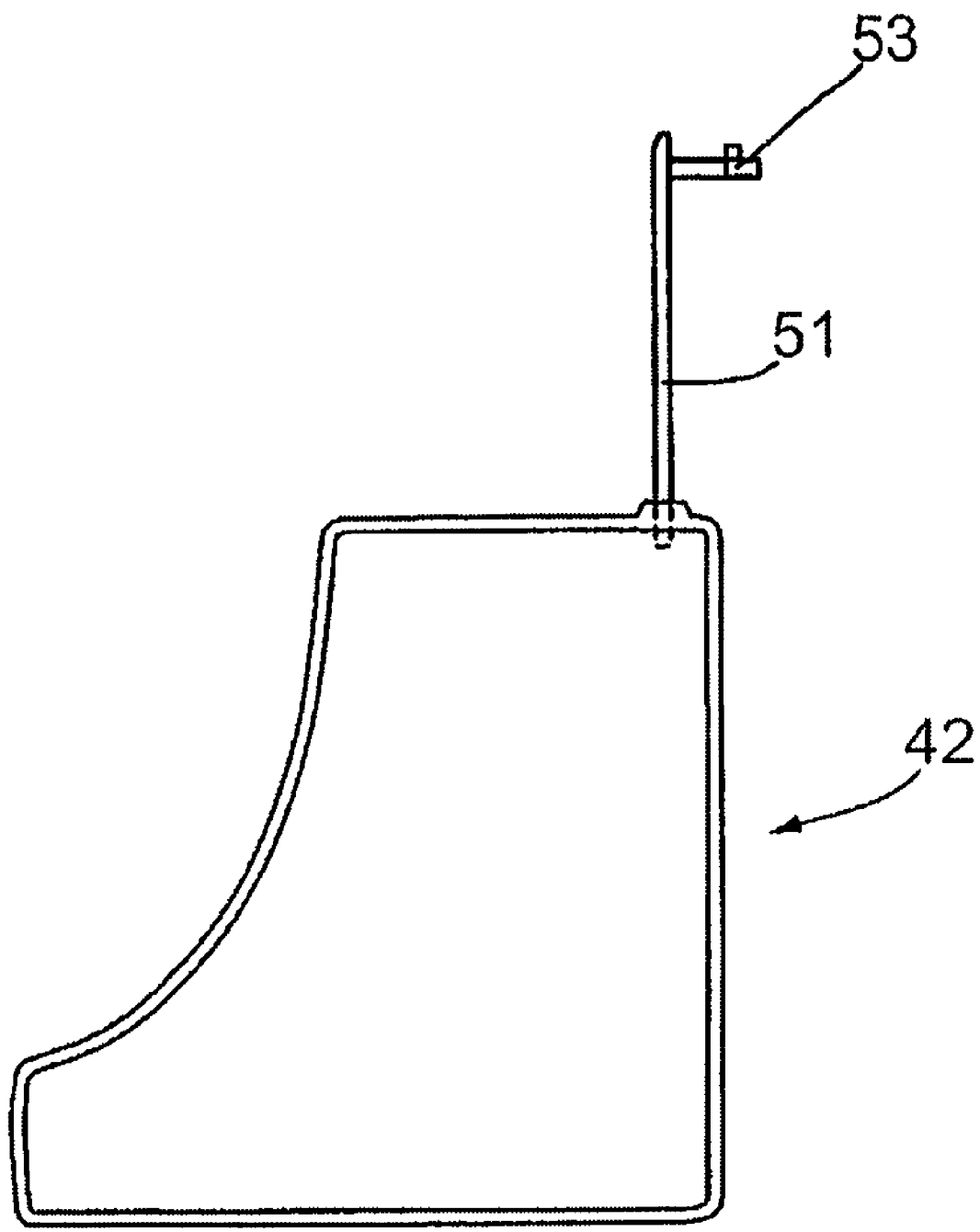
FIG. 18 is a side view of an air cell and hose connector that can be used in the walking brace of FIGS. 1 to 3.

Preferably the walking brace is provided with one or more inflatable, plastic liners or air cells described below. These air cells 42 are located in a central or ankle portion 44 of the brace. The area covered by one of these air cells is indicated in part by the dash line 43 in FIG. 3. The air cells can be constructed as illustrated and described in U.S. Pat. No. 5,577,998 issued Nov. 26, 1996 to Aircast, Inc. FIG. 18 illustrates one side of such an air cell 42. It may or may not contain resilient foam as described in that patent. There can be one of these air cells provided on each side of the rear shell section 20 for a total of two of these air cells or there can be a single air cell only which can extend along both sides and the back of the patients ankle. It will be understood that with the use of these air cells, the therapeutic pressure that is applied to the body part can be adjusted, as desired. However, each air cell 42 is made of an imperforate, flexible plastic material that does not allow air to flow from the outer surface of the air cell to the inner surface. Each air cell is made of two sheets of flexible plastic sealed around their perimeter and can have a flexible hose connector 51 extending from the cell to the exterior of the shell. The connector 51 terminates in a closable port 53 and links the interior of the cell to atmosphere. The connector is made of flexible plastic tubing. A closeable sealing device is provided at the port 53 to trap air in the cell.

The present walking brace 10 is provided with a liner section in the region of these air cells which is able to provide adequate air circulation to the central portion of the brace. In particular, in this region, the liner has two, spaced apart layers of flexible material, including an inner layer 46 and an outer layer 48, which can be seen clearly in FIG. 3. These layers extend substantially parallel to each other in a non-stressed state, for example, when the brace is not being used and there is no pressure being applied to the inner surface of the liner by a person's lower leg, including his or her ankle. Because these layers are preferably made of a flexible, elastomeric material, they will of course bend and distort to some extent when the brace is being used in order to conform to and match the contour of the person's lower leg, ankle and foot. The liner in the central portion of the brace also includes spacer members 50 which are most clearly visible in FIG. 3. These members 50 are arranged between and connect the inner and outer layers and they form air passageways 52 between adjacent spacer members so that air can pass along said passageways to allow air circulation in and through this central portion of the liner during use of the brace. The spacer members can take a wide variety of forms and are not limited to the versions illustrated in the drawings. For example, a variety of suitable spacers are illustrated and described in the applicants copending Canadian patent application No. 2,467,154 filed May 12, 2004.

Figure 6:
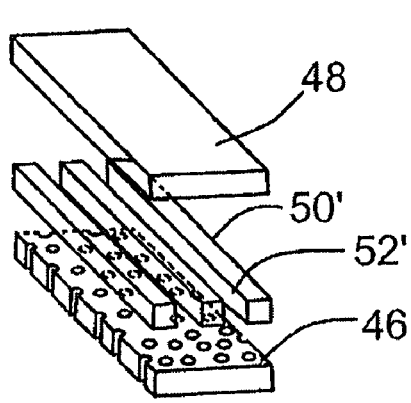
FIG. 6 is an isometric, exploded view showing a small portion of individual components of a preferred venting device.
Figure 8:
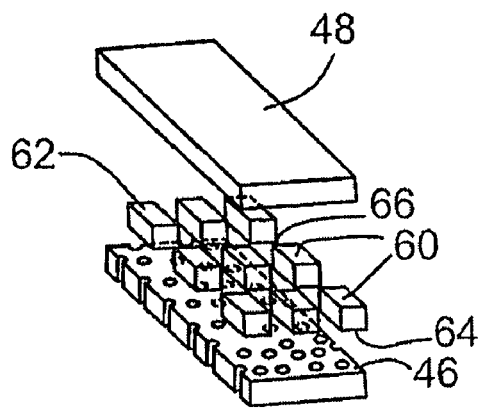
FIG. 8 is an isometric exploded view showing a small portion of components for an alternative form of venting device.
Figure 7:
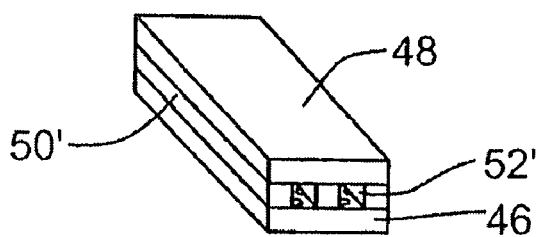
FIG. 7 is an isometric view showing the venting device of FIG. 6 with the components assembled and connected.

With reference now to FIGS. 6 to 8 of the drawings, there is shown therein two different versions of liner construction for the central portion of the brace, both of these versions employing the aforementioned inner and outer layers, with at least the inner layer 46 being porous. Although the outer layer 48 could also be porous, it is preferably imperforate in the region of the air cell 42 which itself is imperforate. In this way the circulating air in this section of the liner is directed through the inner layer 46. In one preferred embodiment of the two layer liner, the layers are approximately $\frac{1}{8}^{th}$ inch apart. As indicated, the preferred material for the inner layer 46 is EVA and this material can also be used for the outer layer 48, if desired. Another porous, elastomeric material that can be used for at least the inner layer 46 is sold under the trademark Nyplex™.

In the embodiment of FIGS. 6 and 7, the spacer members between the layers are elongate, parallel spacer members 50' that are spaced equal distances apart as shown. These members 50' can extend from one side edge of the rear shell section 20 to the opposite side edge and the air passageways 52' formed between the spacer members can be open ended at both ends to allow maximum air circulation. Generally, the number of spacer members provided should be such as to prevent collapse of the air passageways formed between them during use of the venting device. Although it is possible that the air passageways 52' can be open ended at only one side of the brace, it is preferable for both ends of these passageways to be open.

In the variation of the venting device shown in FIG. 8, the spacer members 60 comprise a plurality of relatively small blocks (preferably solid) arranged in a plurality of parallel longitudinal rows. The preferred blocks have flat top sides 62 and flat bottoms 64 making them easier to bond to the adjacent layers by means of a suitable adhesive. An advantage of using these small blocks 60 as spacer members is that the air gaps 66 formed between the blocks in each row permit air circulation in the direction perpendicular to the length of the blocks. Also, by using these blocks, the ability of the venting device to bend in order to conform to the interior of the shell 12 can be enhanced. It will be understood that the spacer members 50, 50' and 60 can be constructed from a variety of flexible materials, including flexible plastics. In one preferred embodiment, the spacer members are also made of ethyl vinyl acetate (EVA) so that they will bend and stretch in the same manner as the inner and outer layers 46, 48 (assuming the latter are made of the same material).

A variety of "EVA" type products are available and can be used in the construction of the double layer venting device in the brace. These include Volara 4E™, Aliplast™ (both of 23 durometer), P-Cell™ (20 durometer for diabetics), and Microcell Puff™ (25 durometer). Another suitable, flexible material for this venting purpose is Poron™, a medical 4708 urethane polymer.

Turning now to the construction of the bottom of the walking brace 10, the user's sole is supported by a rigid base plate adapted for mounting in the walking cast and shaped and sized to support firmly and comfortably at least a major portion of a sole of the user's foot. This brace plate can be made of a variety of substantially rigid supporting materials, including cork and a strong plastic. As shown dearly in FIG. 2, the preferred plate 65 has a network of open topped air passageways 66 formed in its top surface 68. The base plate also has aperture means for allowing air to flow into and out of these air passageways when the base plate is mounted in the walking cast. The illustrated aperture means comprises several apertures 70 formed in the front ends of lengthwise extending passageways 66. The base plate 65 is also referred to herein as a rigid sole member.

The walking brace is also provided with an inner, flexible sole layer 72 covering the rigid sole member 65. This sole layer which can also be made of EVA, if desired, is perforated with numerous small air holes 74 to permit air to flow between the air passageways 66 and a top surface 76 of the sole layer.

The sole layer 72 should be sufficiently strong and rigid to bridge over the air passageways 66 while at the same time being sufficiently flexible and elastomeric to provide a comfortable surface for the sole of the user's foot. It should also have sufficient strength that it is not pushed down into the passageways 66 by the weight of the user's foot in a manner which would block the air flow through the passageways 66.

Figure 9:
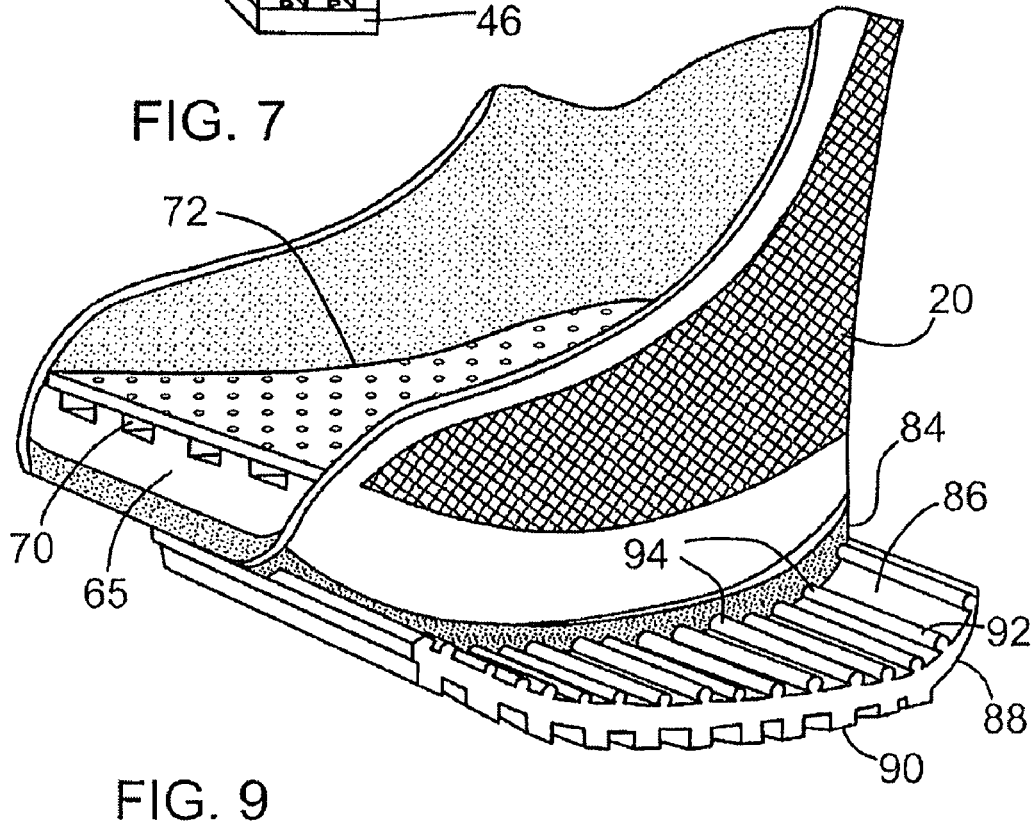
FIG. 9 is a perspective view of a bottom section of a walking brace of the invention, this view showing a detachable foot piece partly removed from a bottom section of the brace.

The bottom surface 80 of the base plate 65 can be rounded to form a convex curve from toe to heel as shown or it can be flat. In any event, its shape must match that of an adjacent surface 82 of a further support layer 84 on top of which the base plate 65 can be mounted. The layer 84 can be made of a suitable, wear resistant plastic or rubber material which optionally can be reinforced, if desired. In a particular preferred embodiment of the walking brace, there is a detachable foot piece 86 which can be made of a tough, elastomeric material and which is mounted on the foot section of the brace, for example, on the bottom of the support layer 84. This foot piece 86 preferably has a bottom surface 88 which is adapted to engage the ground during use of the brace, for example, by having a plurality of gripping ribs or ridges 90 formed thereon. The detachable nature of the foot piece 86 is illustrated in FIG. 9 wherein the foot piece has been partially removed from the bottom of the foot brace by transverse, sliding movement. Although the foot piece 86 can be detachably connected to the brace in a variety of ways, the illustrated foot piece has a number of parallel, transverse connectors 92 formed integrally on the top surface. These slide into and out of respective grooves 94 formed along the bottom of the support layer 84 and constructed to capture the connectors 92, which can have a rounded transverse cross-section. In order to maintain the foot piece 86 in its normal position for use, a friction fit can be provided between the connectors 92 and the surface of the grooves 94. Alternatively, a mechanical connector, such as a locking pin or one or more short screws can be used to hold the foot piece 86 securely in place. A particular advantage of having a detachable foot piece of this type is that, when it is not required, for example for sleeping or resting, the foot piece can be removed by the patient to make the walking brace lighter and more comfortable for such purposes. Of course, it will be understood by those skilled in the art that it is not necessary to have a detachable foot piece 86 and, for example, the bottom layer of the walking brace can be simply the support layer 84 made with a suitable bottom surface.

The walking brace 10 of FIG. 1 is also provided with two, three or more connectors for securing the brace on the body part. Shown in FIG. 1 are two preferred Velcro™ type strap connectors 96 and 98. These strap connectors can be similar to or the same as those illustrated and described in the aforementioned U.S. Pat. No. 5,577,998. Each strap connector is provided with a strong, plastic buckle 100 at one end. Provided on one side of the strap along an elongate section 102 are numerous fiber loops forming the loop portion of the Velcro fastener. An end section 104 of each strap is covered on one side with numerous small plastic hooks forming the hook portion of the Velcro fastener. These small hooks can be formed on the same side of the strap as the loops on the strap section 102. It will be understood that each strap can be secured in the usual fashion to hold the front shell section 18 in place and to apply pressure to the leg or foot by inserting an end 106 of the strap through a hole formed in its respective buckle 100 and then pulling the strap tight by pulling the end section 104 back along the section 102 and attaching the hooks to the loops. Although only two strap connectors are shown in FIG. 1, it will be understood that a third strap connector can be provided on the foot section 110 of the brace. This strap connector can be constructed in a similar manner to the strap connectors 96 and 98 (except that it is divided into separate buckle and Velcro™ sections) and operates in a similar fashion to press the horizontally extending portion of the front shell section against the top of the users foot. Also, although not visible in the drawings, each strap connector can be held in place by one or two suitable pin connectors which connect the respective strap or strap section to the rear shell section 20. In the case of the two upper strap connectors 96, 98, a single pin connection can be provided for each in the centre of the back of the shell section.

In order to prevent the strap connectors (which can be quite wide) from interfering with the air circulation through the exterior shell, strap bridges can be provided as shown in FIGS. 1 to 3. The rear shell section 20 can have two, curved plastic bridges 112 and 114 that extend completely around the two sides and back of this shell section. Each bridge can be formed with outwardly projecting edge flanges 116 and 118 that help to hold the respective strap in place as and when it is secured around the exterior shell. Each bridge is supported at spaced apart locations to elevate its inner surface above the exterior surface of the rear shell section. In particular, bridge supports 120 and 122 are provided at opposite ends of each of these bridges and connect the bridge span to each front edge section of the rear shell. It will be understood that one or more additional bridge supports can be provided along the length of each bridge between the end supports 120 and 122. No bridge need be provided in the foot section of the rear shell section 20 since each of the two sections of the strap (not shown) for the foot section can simply be connected to the top edge section of the rear shell in this region.

Also, there can be provided three bridge sections 125 to 127 on the front shell section 18. Again, the span of each of these bridge sections is spaced from the front, perforated surface of the front shell section. This gap can be seen dearly at 128 below the bridge section 127 in FIG. 1. Again, the span of each bridge section is supported in an elevated position by bridge supports 130 and 132 located on opposite ends of the span. Preferably the bridge sections 125 to 127 can be provided with edge flanges 134 and 136 to help maintain the secured strap connector in place on the bridge section.

Figure 5:
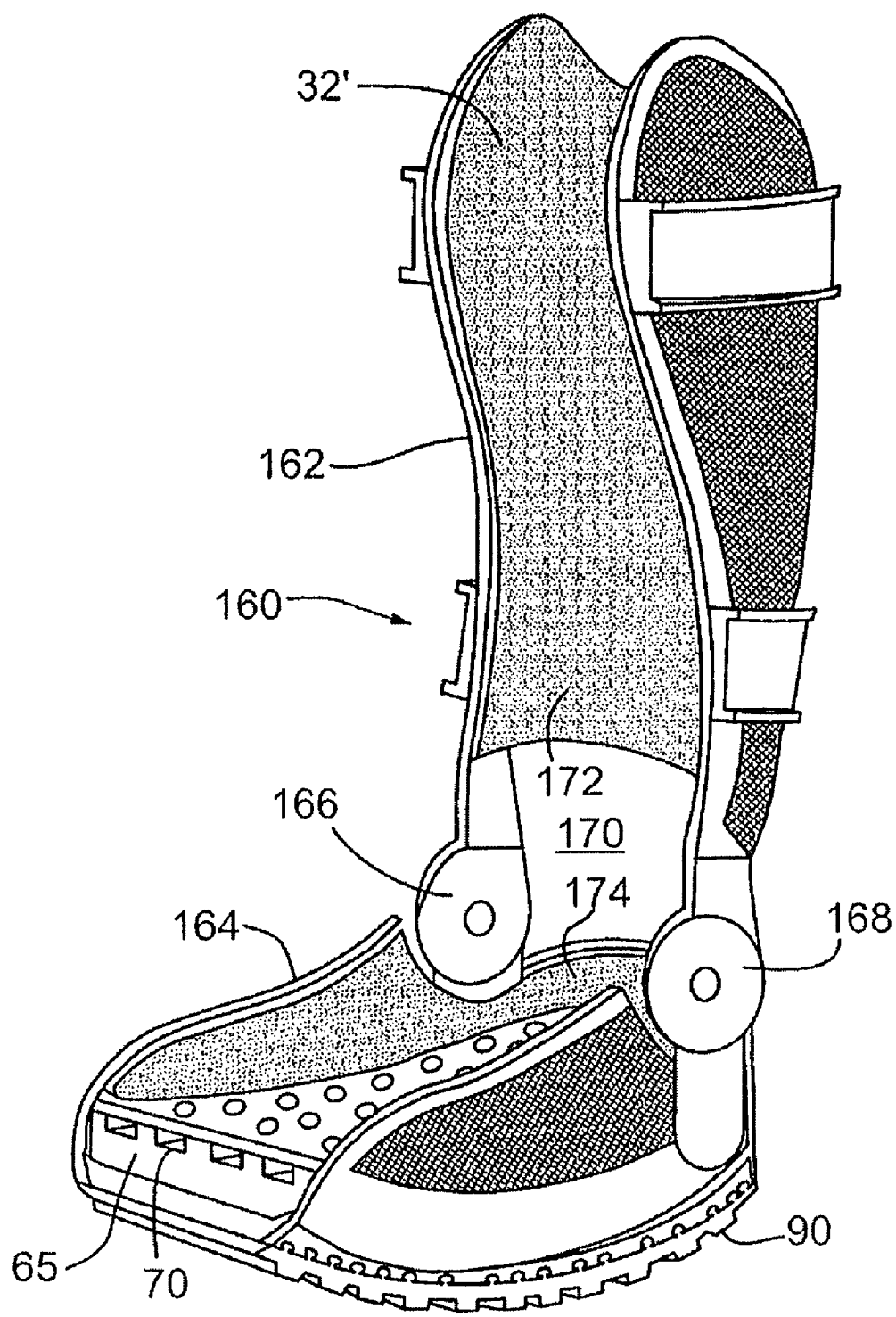
FIG. 5 is a perspective view showing the front and left sides of a second embodiment of walking brace, its frontal shell also being omitted for sake of illustration.

Turning now to FIG. 5, there is illustrated therein an alternative form of walking brace indicated generally at 160. This walking brace can be constructed in a similar manner to walking brace 10 of FIG. 1, except for the differences noted hereinafter. It will be appreciated that, although not shown in FIG. 5, this walking brace is also equipped with three or more strap connectors similar to those shown in FIG. 1 to secure the brace on the lower leg and foot of a patient. A primary difference between the brace 160 and the brace 10 of FIG. 1 is that this brace has a lower leg section 162 and a foot section 164 which are pivotably connected to one another by two pivot joints 166 and 168. The lower leg section, which in use extends generally vertically, is adapted to cover at least a portion of a person's lower leg above his or her ankle. A major portion of the person's foot rests on the sole layer 72 of the foot section. In the illustrated brace 160 there is an open area 170 located at the rear of the users ankle and extending between the two pivot joints. It will be understood that pivot joints 166, 168 of the type illustrated are per se known in the walking brace art and according a detailed description herein is believed unnecessary. The purpose of these pivot joints is to permit the operating angle of the foot section (as defined by the top of layer 72) to be adjusted by the medical personnel relative to the generally vertical position of the lower leg section 162. For example, in the case of some injuries, it may be necessary for the patients-foot to initially extend at a downward angle to the normal horizontal position and the brace 160 can be set at a position which permits this. Once the brace has been set in the required position, a known securing mechanism is provided that prevents further pivotal movement at the joints 166, 168. Later, after the injury has had some time to heel, the relative angle of the foot section can be adjusted again by the doctor or other medical practitioner. In such case, the foot section can be pivoted to a position that will bring the user's foot closer to or to the normal horizontal position.

It will be further understood that the walking brace 160 is not equipped with any air cells 42 in the ankle region of the brace. Accordingly, the liner 32' in this embodiment can comprise a single layer of flexible, porous material, such as perforated EVA. In this case, the liner 32' comprises at least two separate sections, including an upper section 172 covering the inside surface of the lower leg section 162 and a lower section 174 which can include a strip around the back of the heel.

Figure 10:
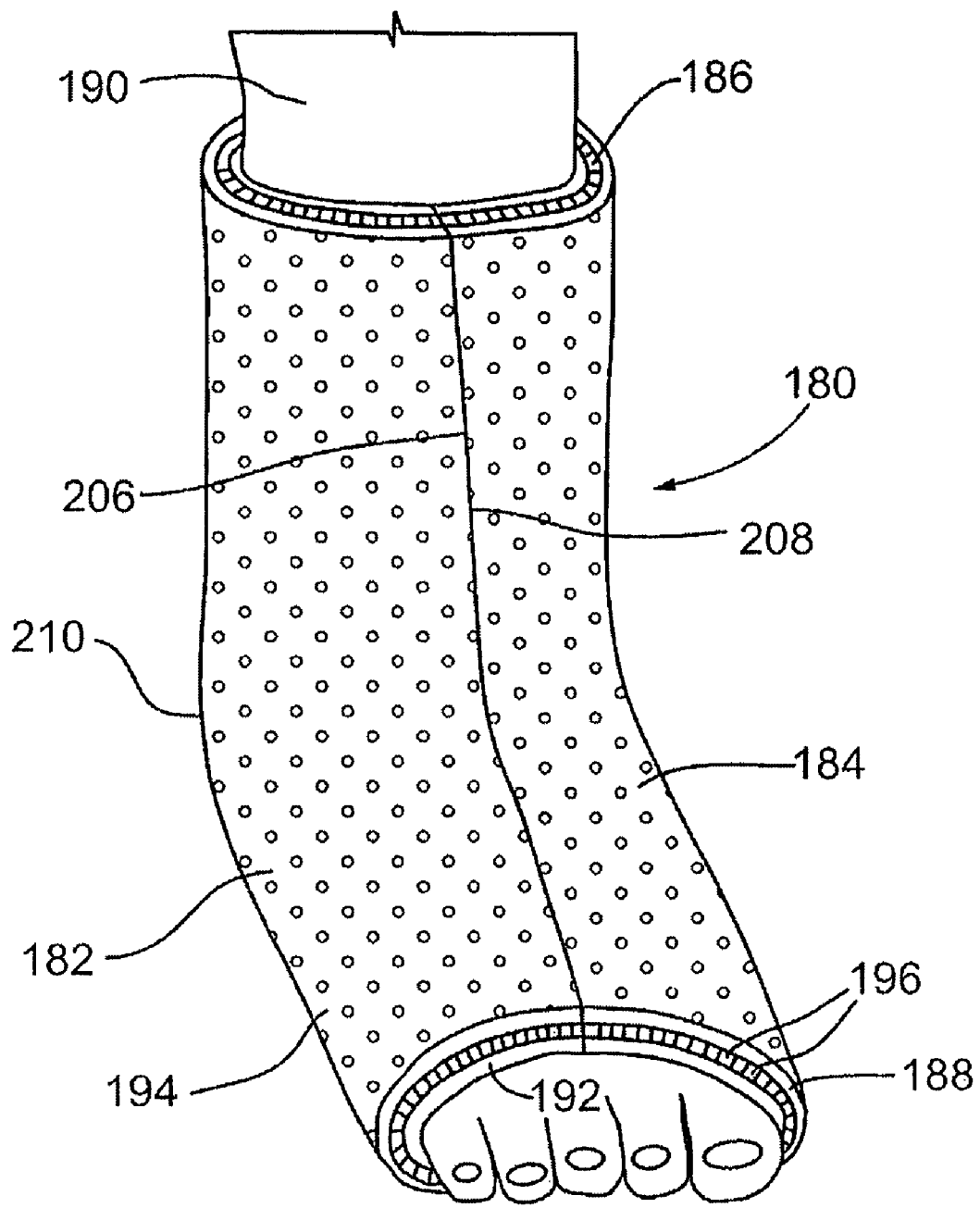
FIG. 10 is a perspective view showing the front and right sides of a venting device for an orthopedic cast, this device being shaped to fit around the foot and ankle of a patient.
Figure 11:
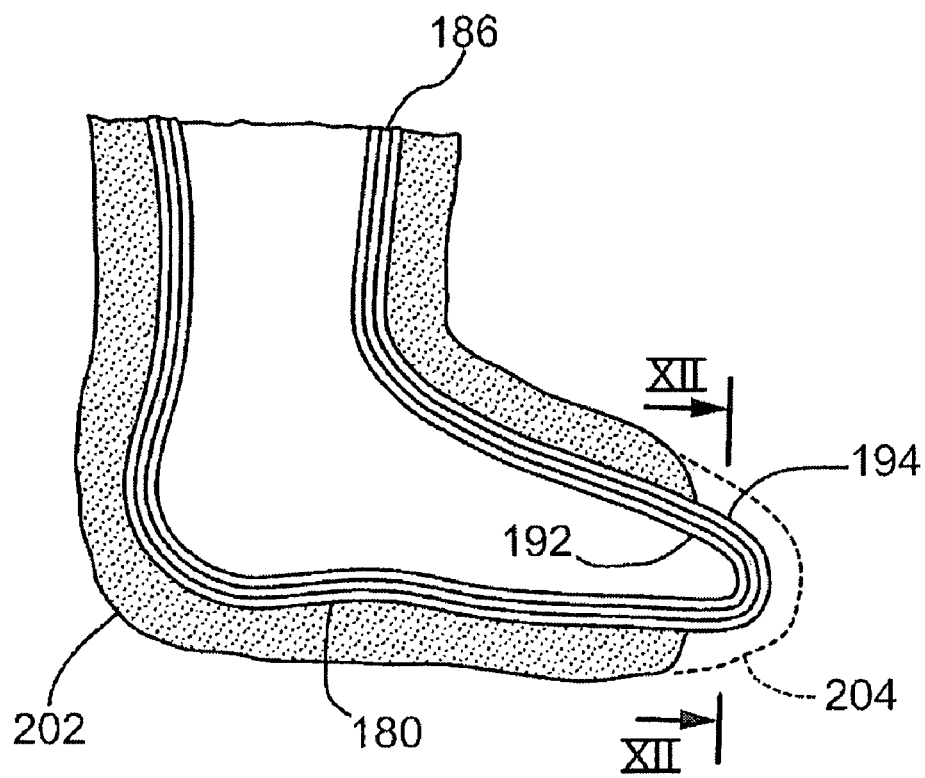
FIG. 11 is a vertical cross-section of a venting device extending around a patient's foot and ankle, with a rigid cast extending around the venting device.
Figure 12:
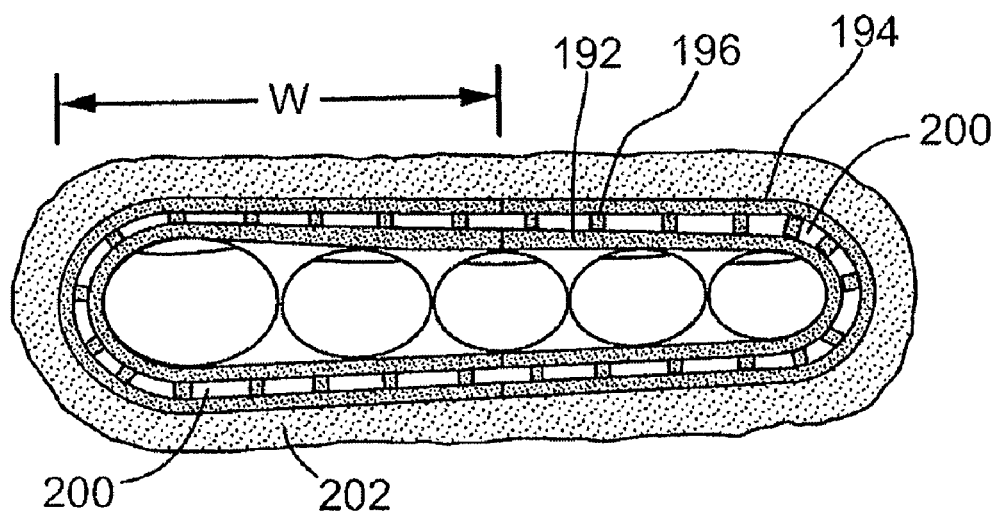
FIG. 12 is a vertical cross-section taken along the line XII-XII of FIG. 11 and showing the patients five toes surrounded by the venting device.

FIGS. 10 to 12 illustrate a venting device 180 constructed according to another aspect of the invention. This venting device can be used with an orthopedic cast or brace, including a walking brace. The venting device comprises two half sections 182 and 184 which form a complete venting device when combined together to enclose a person's or animal's body part. In FIGS. 10 to 12, the illustrated body part is a person's ankle, including at least most of the person's foot. Each half section has a length extending from one end 186 thereof to an opposite end 188 thereof and a width W (indicated in FIG. 12) which can vary. Each half section is preformed, for example, by a heating and shaping procedure, so as to fit closely around a respective curved side of a particular body part, for example, the curve side 190 of the lower leg.

Each half section comprises two spaced-apart layers of flexible resilient material that extend substantially parallel to each other. Thus, there is an inner layer 192 and an outer layer 194. The resilient material of at least the inner layer 192 is porous although it is possible for both layers to be porous as illustrated in FIG. 10. As in the venting devices illustrated in FIGS. 6 to 8, the venting device 180 also has spacer members indicated at 196 arranged between and connecting the two layers 192 and 194. The spacer members form numerous air passageways 200 between adjacent spacer members so that air is free to pass along these passageways from one or more open ends of the passageways located at least one of the two ends of the respective half section. In the venting device 180 of FIG. 10, these passageways are open at both the end 186 and the opposite end 188, thereby allowing good air circulation.

FIG. 11 illustrates a variation of the venting device 180 covered by a rigid plaster or fiberglass cast 202. The venting device 180 of FIG. 11 differs from that shown in FIG. 10 in that the device covers the toes of the foot (a version used if the cast itself covers the toes). The cast can either be formed as shown in solid lines so as not to cover the toes of the patient or it can be extended as indicated by dash line 204 to cover the toes of the patient. In the latter case, unless provision is made for forming openings in the cast, then the passageways formed by the venting device 180 are open only at upper end 186. Also, it will be understood that when this venting device 180 is used, the two half sections 182, 184 are placed around the selected body part so that they meet along respective lengthwise extending edges 206 and 208 and surround the body part. Once the venting device is in place, the cast or brace is applied over the venting device as shown in FIGS. 11 and 12 so that the venting device is pressed against the body part and the cast or brace.

In the illustrated preferred embodiment of this venting device, each half section 182, 184 is substantially U-shaped in widthwise cross-section (as can be seen clearly in FIG. 12), although the shape of the U can vary substantially depending upon the section of body being covered. It will also be seen that each half section 182, 184 is bent at 210 in the lengthwise direction, for example, in the region of the ankle. It will be appreciated that this particular form of venting device is particularly useful where a venting device is required that extends around a bent body part such as an ankle or elbow.

Figure 16:
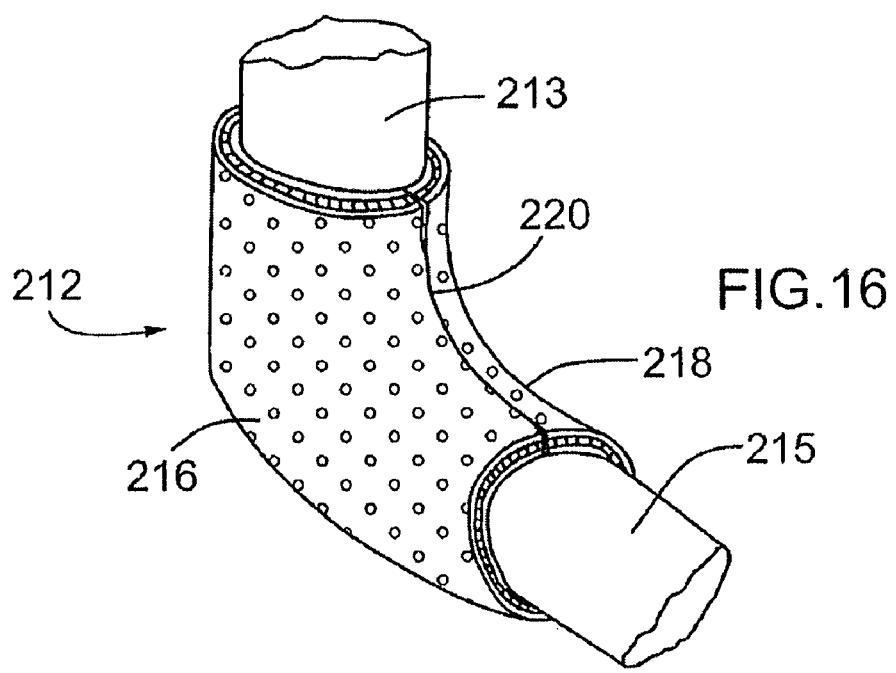
FIG. 16 is a perspective view showing the top, front and right sides of a venting device for a cast, this device being fitted around a person's elbow in a bent position.

FIG. 16 illustrates another venting device formed and sized to fit around a patient's elbow connecting upper arm section 213 to forearm 215. As in the venting device of FIG. 10, the venting device 212 also comprises two half sections 216 and 218 which join along lengthwise extending edges located at 220.

Figure 17:
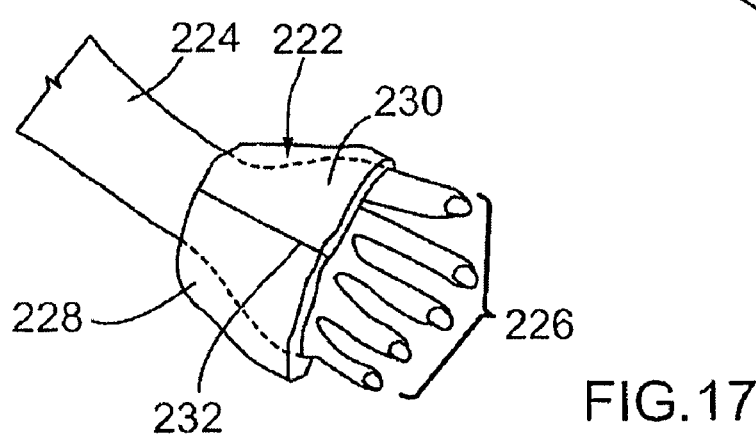
FIG. 17 is a perspective view showing the top and front end of another version of a venting device for a cast, this version being fitted around a person's wrist area.

FIG. 17 illustrates another embodiment of venting device 222 which is shaped and sized to fit the curved surface of the wrist region formed between forearm 224 and fingers 226. Again, this venting device 222 is constructed in a manner similar to the venting devices 180 and 212 and comprises two half sections 228 and 230 that are joined along lengthwise edges at 232.

It will be appreciated that the venting devices 180, 212 and 222 can all be constructed using two flexible layers in the manner illustrated in FIGS. 6 to 8. Again, a preferred material for the inner layer 192 is ethyl vinyl acetate (EVA) formed with numerous, small perforations distributed over its inner and outer surfaces and the same material can also be used for the outer layer 194, although there is no need for the outer layer to be perforated in the case of a venting device for a cast. The spacer members 196 can be similar in their construction and layout to the spacer members 50' shown in FIG. 6. That is, they can be solid, elongate members that extend in the lengthwise direction of their respective half section. Of course, it is not necessary for the spacer members to extend the entire length of the half section but there can be two, three or more elongate spacer members aligned with one another, separated by suitable gaps and together extending from one end 186 of the half section to the opposite end 188.

As indicated, another suitable, flexible material for the inner and outer layers is Nyplex™.

It will be understood that the venting devices 180, 212 and 222 can either be custom formed so as to fit snuggly around a particular patient's body part, or they can be preformed in a number of standard sizes so that the medical practitioner or doctor must select a particular, available size that fits his patient's body part sufficiently closely. It will, of course, be understood that if a chosen preformed venting device does not initially fit sufficiently close around the body part, it generally is possible to trim one or more half sections so that that when the two half sections are combined, a sufficiently close fit is obtained.

One available procedure for manufacturing a venting device such as that shown in FIGS. 10 to 12 is to shape a single layer, for example, the inner layer of the venting device, on a suitable mold and, once shaped as required, to heat the layer to a suitably high temperature that the layer takes on the shape of the mold and retains this shape once cooled. Spacer members are then applied to the shaped layer in the desired manner, forming the required air passageways between them. Then a second layer of flexible material, normally the outer layer, is added, and is connected, for example, by adhesive, to the spacer members. This outer layer can then be suitably heated so that it also will tend to retain the required shape. The two halves of the venting device can be made in this manner and, once completed, they are placed around the body part so that they meet along their respective lengthwise edges as shown in FIGS. 10, 16 and 17.

Figure 13:
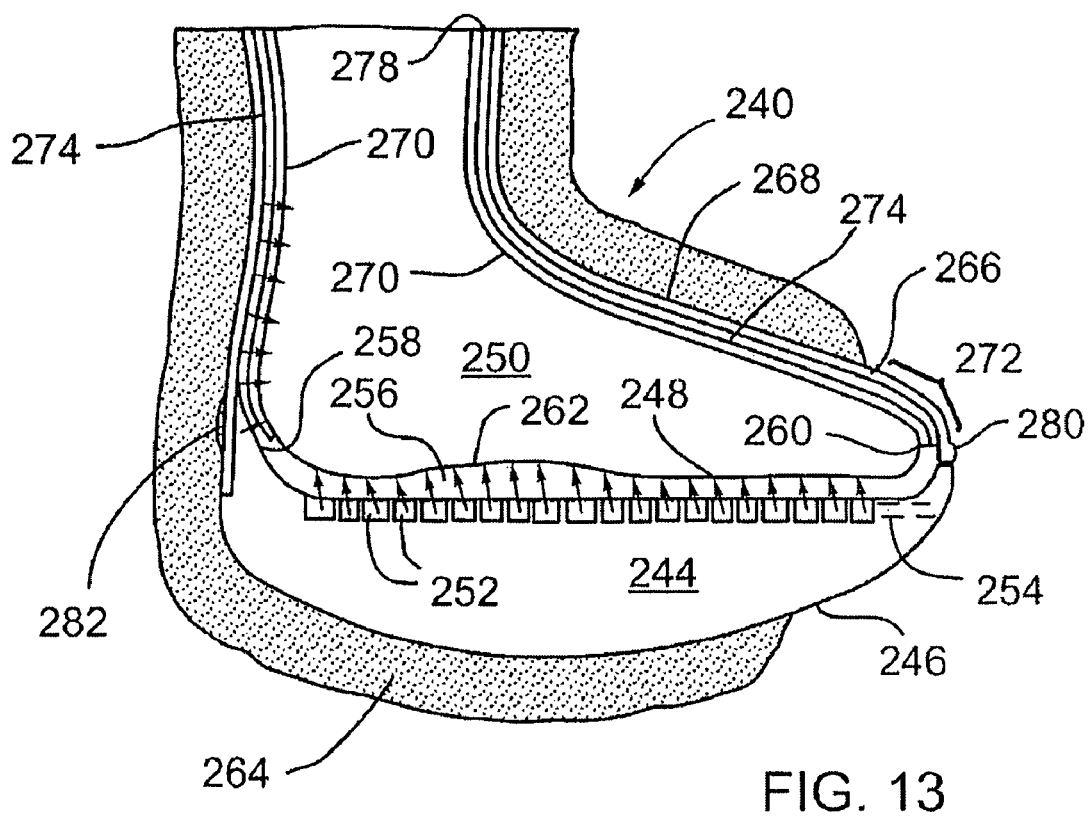
FIG. 13 is a vertical cross-section of a walking cast using a supporting and ventilating device constructed according to another aspect of the invention.
Figure 14:
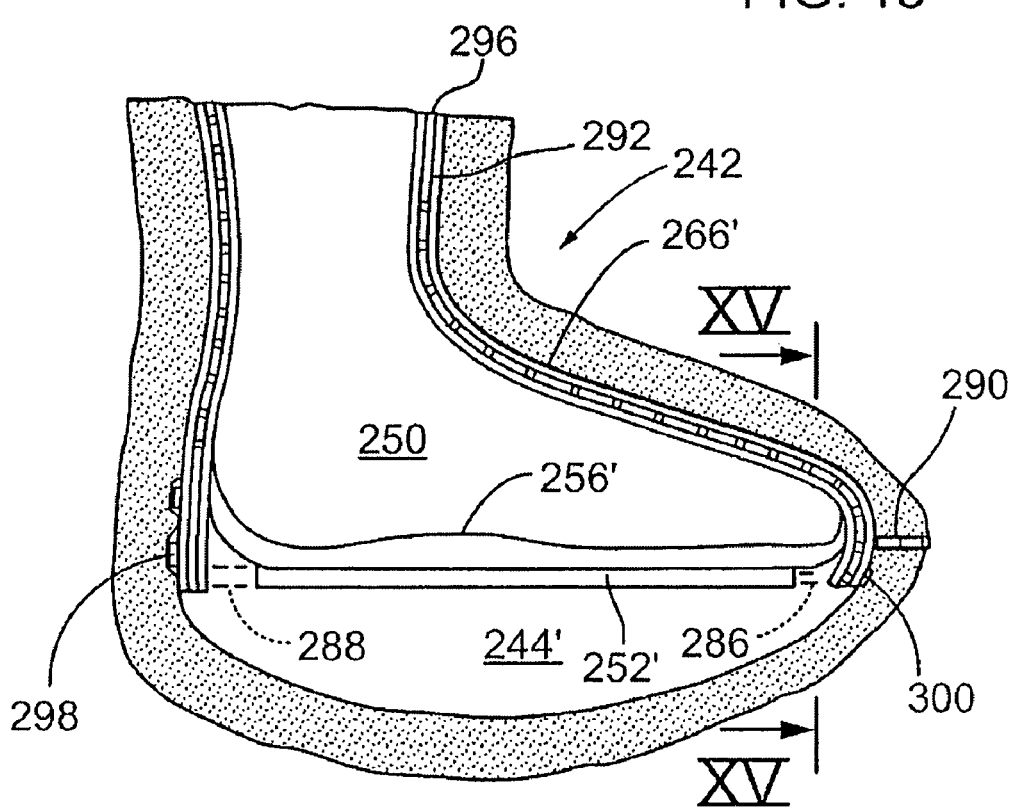
FIG. 14 is another vertical cross-section of a walking cast wherein the front of the foot is covered by the cast.

Turning now to the ventilated casts shown in FIGS. 13 and 14, these are both walking casts provided with a supporting and ventilating device constructed in accordance with a further aspect of the invention. The walking cast 240 of FIG. 13 is open at the front so that the patients toes and a portion of the venting device project from the front end of the cast. In the walking cast 242 of FIG. 14, the front end of the cast is substantially enclosed. The supporting and venting device includes a rigid base plate 244 in the cast of FIG. 13. This base plate has a bottom surface 246 which forms a convex curve from its heel end to its toe end. This base plate is shaped and sized to support firmly at least the major portion of a sole 248 of the foot 250. The base plate has a network of open topped air passageways 252. These passageways can, for example, comprise several longitudinally extending passageways that connect the illustrated transversely extending passageways. Alternatively, the passageways can be laid out in the manner of the passageways 66 shown in FIG. 2, if desired. Several air passageways (indicated in dash lines) can be provided at 254 to connect the passageways 252 to the front surface of the base plate, thus allowing air to circulate into and out of the passageways 252 when the base plate is mounted in the walking cast.

Mounted on top of the base plate is a flexible sole layer 256 which can either be flat or contoured (as shown) to fit the contour of the sole of the foot. This sole layer extends from a rear end 258 located at the heel of the user to a front end 260 located at the toe of the user. If desired, the sole layer can be turned up at each end as shown. The sole layer is adapted to cover substantially the top surface of the base plate and it is porous to permit air to flow between the air passageways 252 and a top surface 262 of the sole layer. Preferably the sole layer 256 is elastomeric and is made of ethyl vinyl acetate (EVA). One preferred material for the base plate is a suitable rigid plastics material. It will also be seen that with this walking cast arrangement, the base plate is substantially covered and supported by the bottom of the cast at 264.

The supporting and ventilating device of FIG. 13 includes a flexible venting arrangement indicated generally at 266 connected to the base plate 244 and adapted to cover at least a top and sides of the foot 250 prior to application of the cast material to form the walking cast. The preferred venting arrangement 266 is capable of circulating air to at least the top and sides of the foot and includes two, substantially parallel layers of flexible material at 268 and 270. At least the inner layer 270 is perforated and the preferred material for this inner layer is EVA. The outer layer 268 can also be perforated EVA material. By using perforated material for the outer layer (at least in the toe region), air is able to circulate between the two layers and to exit from and enter into the passageways formed between the two layers in the frontal region indicated at 272. In this frontal region, a front section of the outer layer 268 projects from the front end of the rigid cast. Located between the two layers 268 and 270 are a number of elongate spacer members 274. These spacer members can be made of EVA or Nyplex™ and preferably they extend in the lengthwise direction from top end 278 to the bottom end of the venting arrangement. In this way, air is able to flow through the passageways and reach the inner layer 270. This venting arrangement can be attached by stitches located at 280 and 282 to the base plate.

Again, it will be understood that a variety of different types of spacer members can be used to separate and connect the inner and outer layers of the venting arrangement 266. For example, the spacer members can be similar to the spacer blocks 60 shown in FIG. 8.

Figure 15:
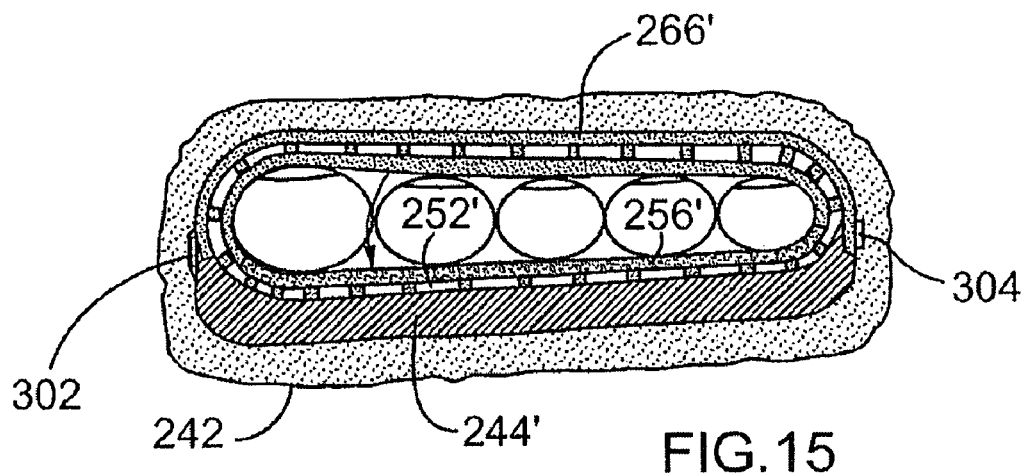
FIG. 15 is a transverse vertical cross-section of the walking cast, this view being taken along the line XV-XV of FIG. 14.

The walking cast shown in FIG. 14 is similar in its construction to that of FIG. 13, except for the differences noted. In this case, the rigid cast material substantially encloses the supporting and ventilating device, including a rigid base plate 244'. In FIG. 14 there is shown a lengthwise extending passageway 252' and it will be understood that there can be a plurality of these lengthwise passageways spaced apart from one another and interconnected by transversely extending passageways such as those illustrated in FIG. 13. Short, interconnecting passages can be provided at 286 and 288 to connect the ends of the network of passageways 252' to the passageways formed by the flexible venting arrangement 266'. Additional air can be provided through optional frontal holes located at 290 which extend through the cast material to a front end section of the venting arrangement. Again, a flexible sole layer 256' covers substantially the top surface of the base plate and this sole layer is porous to permit air to flow between the air passageways 252' and the top surface of the sole layer. The spacer members 292 illustrated in FIG. 14 are relatively short blocks similar to the blocks 60 of the venting device illustrated in FIG. 8. These blocks permit air to enter and exit through the top end of the venting arrangement indicated at 296. Stitching can be provided at 298 and 300 to connect bottom end sections of the venting arrangement to the base plate. As illustrated in FIG. 15, stitching can also be provided at 302 and 304 along the sides of the base plate in order to connect the venting arrangement along the sides. For this purpose, the left and right side edges of the base plate can be turned upwardly as shown to facilitate stitching.

An optional feature of the walking brace of FIGS. 1 to 3 is the use of strong plastic or metal connecting cables 306 and 308. These can be used at both the top and bottom of the brace in order to securely connect the front shell section 18 to the rear shell section 20. The cables extend through holes provided in these shell sections on the left and right edges of the shell sections. The purpose of these optional cable connectors is to ensure that the front shell section is not removed except under medical supervision and except when authorized. It may be desirable, for example, to prevent the patient from inadvertently or otherwise removing the front shell section on his own and thereby injuring himself when the brace is removed. This type of cable connector is well known in the connector art and a detailed description herein is therefore unnecessary.

It will be appreciated that it is also possible to construct footwear incorporating features and principles of the walking braces described above. In particular, footwear in the nature of work shoes and safety shoes can be constructed, which includes an exterior shell adapted to fit around at least the foot of the person having interior and exterior surfaces. This exterior shell can be perforated with a large number of small, closely spaced perforations in a manner similar to the orthopedic braces shown in FIGS. 3 and 5. These perforations can extend over a substantial portion of the interior and exterior surfaces so as to allow air to pass through the shell between the surfaces. Also, the footwear can be provided with an interior liner arranged in the shell which can be either rigid like the above described braces or somewhat more flexible to make the shoe or boot more comfortable to wear. This interior liner would cushion at least the foot of the user and, if the footwear is a boot that extends up the lower portion of the leg, the interior liner can be extended to also cushion the lower leg inside the shell. The liner is perforated over at least a substantial portion thereof so as to allow air to pass between the inner and outer surfaces of the liner. Unless the footwear is equipped with an inflatable air cell, the liner can be a single layer of an elastomeric material such as the above described ethyl vinyl acetate (EVA). The perforated liner allows the air include at least one fastener for securing the footwear on the foot, for example, a buckle, boot lace or Velcro™ type straps.

The aforementioned footwear constructed in accordance with the invention can also include a shell that has a rigid base plate adapted and arranged to support the sole of the foot. This base plate and its respective liner can be similar to that illustrated and described above in connection with FIGS. 3, 5 and 9. The preferred base plate would also have a network of open topped air passageways formed in a top surface thereof and apertures for allowing air to flow into and out of these air passageways when the footwear is being worn on the foot. The aforementioned footwear liner can include a flexible sole layer covering the top surface of this base plate, this sole layer being porous to permit air to flow between the air passageways and a top surface of the sole layer.

It will be readily apparent to one skilled in the art of orthopedic braces, casts, and footwear that various modifications and changes can be made to the illustrated and described braces, casts, venting devices and footwear without departing from the spirit and scope of this invention. Accordingly, all such modifications and changes as fall within the scope of the appended claims are intended to be part of this invention.

I claim:

1. A walking brace for providing therapeutic pressure to a person's lower leg, said brace comprising:
   a rigid exterior shell adapted to fit around at least a major portion of said lower leg and having interior and exterior surfaces and two opposite sides, said shell being perforated over a substantial portion of each of said interior and exterior surfaces so as to allow air to pass through the shell between said surfaces;
   an interior liner arranged in said shell to cushion said major portion of said lower leg, said liner including two, spaced-apart, inner and outer layers of flexible material that extend substantially parallel to each other and spacer members arranged between and connecting said inner and outer layers, at least said inner layer being porous so as to allow air to pass through the inner layer, said spacer members forming air passageways between adjacent spacer members so that air can pass along said passageways to allow air circulation in said liner and through said inner layer during use of the brace;
   at least one strap connector for securing said brace on the lower leg; and
   a strap bridge for each of said at least one strap connector, said strap bridge being mounted on said exterior shell by means of bridge supports located at least at opposite ends of the bridge and being adapted to support its strap connector away from the exterior shell, said bridge including a bridge span extending between said bridge supports and around the two opposite sides and spaced from said exterior surface of the exterior shell,
   wherein during use of said walking brace, each of said at least one strap connector extends over and is supported by its respective strap bridge in such manner that air is able to circulate through said exterior shell under each of said at least one strap and its respective bridge.

2. A walking brace according to claim 1 wherein said exterior shell includes a rigid, front shell section adapted to cover a front area of said lower leg and a top surface of said foot of said person, said liner extends between said front shell section and said lower leg during use of said brace, and said at least one connector is adapted to secure said front shell section to a rear shell section forming a remainder of said exterior shell.

3. A walking brace according to claim 2 including a plurality of said at least one strap connector and additional strap bridges adapted to support their respective strap connectors away from said front shell section and mounted on said front shell section, wherein during use of said brace, at least one of said additional strap bridges is aligned with said first mentioned strap bridge which is mounted on said rear shell section.

4. A walking brace according to claim 2, wherein said rigid exterior shell defines a foot section and a lower leg section interconnected by pivot means.

5. A walking brace as defined in claim 1 further including a sole comprising a rigid base plate having a network of open air passages formed in a surface thereof; and
   a perforate, flexible inner sole overlying the base plate.

6. A walking brace as defined in claim 5 further comprising a foot piece providing a wear-resistant resilient bottom surface with gripping ridges for engaging the ground.

7. A walking brace as defined in claim 6 wherein said foot piece is at least partly detachable from said sole.

* * * * *